United States Patent [19]

Grey et al.

[11] Patent Number: 5,050,588

[45] Date of Patent: Sep. 24, 1991

[54] HIGH ENERGY ULTRASONIC LENS ASSEMBLY WITH MOUNTING FACETS

[76] Inventors: Richard Grey, 1400 Arbor La., Alamo, Calif. 94507; Frank C. Ford, 48 Golf Rd., Pleasanton, Calif. 94566

[21] Appl. No.: 476,874

[22] Filed: Feb. 8, 1990

[51] Int. Cl.[5] .......... A61B 8/00

[52] U.S. Cl. .......... 128/24 AA; 128/24 EL; 128/662.03; 310/311

[58] Field of Search .......... 128/24 A, 24 EL, 660.03, 128/662.03, 804, 399; 310/311, 335

[56] References Cited

U.S. PATENT DOCUMENTS

| | | | |
|---|---|---|---|
| 3,587,567 | 6/1971 | Ziedonis | 310/335 |
| 4,787,394 | 11/1988 | Ogura | 128/24 EL |
| 4,858,597 | 8/1989 | Kurtze et al. | 128/24 EL |
| 4,865,042 | 9/1989 | Umemura et al. | 310/335 |
| 4,955,366 | 9/1990 | Uchiyama et al. | 128/24 EZ |
| 4,960,107 | 10/1990 | Aida et al. | 128/24 A |

*Primary Examiner*—Lee S. Cohen
*Assistant Examiner*—Krista M. Pfaffle
*Attorney, Agent, or Firm*—Paul Hentzel

[57] ABSTRACT

A lens assembly is formed by a curved dish or support member with piezo-electric transducers mounted on the concave outer surface. Flat mounting facets are machined on the outer surface to accommodate bonding between the transducer and the support member. A small concave focusing surface or lens for each transducer is machined on the concave inner surface of the support member directly opposite to the transducer and mounting facet. The focusing lenses are only slightly more convex than the inner surface of the support member, and the size of the focusing lenses is only a fraction of the size of the support member. Therefore, the path length of the energy from every point on every transducer to the invivo target region is almost identical. The energy arrives at the target region very closely in phase, forming a short pulse of maximum intensity.

33 Claims, 4 Drawing Sheets

HIGH ENERGY ULTRASONIC LENS ASSEMBLY WITH MOUNTING FACETS

TECHNICAL FIELD

This invention relates to high energy ultrasonic devices which concentrate ultrasonic energy at an invivo target point for treating concrements and coagulations.

BACKGROUND

Lithotripsy (stone-breaking) machines focus ultrasonic energy at stones (or other internal sites) for eroding the stone down to a size that can be passed by the patient. The ultrasonic energy is generated by piezoelectric crystal transducers mounted on a lens assembly. The transducers are internally stressed or "charged" by an intense electric field and discharged simultaneously to generate a collective pulse of ultrasonic energy.

Heretofore, the crystal transducers were mounted on the back of a flat plate lens assembly which provided a flat mounting face for the transducers. The front of the lens assembly was a single large concave surface designed to focus the ultrasonic energy from all of the transducers at an invivo point within the patient. The simultaneous firing of the transducers promoted an "in phase" relationship between the individual pulse from each transducer, thereby increasing the pulse intensity of the collective pulse.

However, transducers near the edge of the flat plate lens assembly had a longer ultrasound path length to the target region than transducers near the center. As a result of this edge delay, the energy pulses from the peripheral transducers arrived at the target region later. The resulting phase loss reduced the intensity of the collective pulse. A corrective curve for the lens assembly having a generally elliptical or oblate shape was required to correct this peripheral astigmatism. The edge delay could not be corrected by using a simple concave curve with a true spherical shape.

SUMMARY

It is therefore an object of this invention to provide an improved high, energy lens assembly.

It is a further object of this invention to provide such a lens assembly which is more efficient and delivers higher pulse intensity with less operating voltage and lens area.

It is a further object of this invention to provide such an efficient lens assembly which employs a simple curve having a true spherical surface.

It is a further object of this invention to provide such a lens assembly which converges the ultrasonic energy with minimum edge delay.

It is a further object of this invention to provide such a lens assembly that is simpler and less expensive.

It is a further object of this invention to provide such a lens assembly which has a longer service life and is easier to maintain.

It is a further object of this invention to provide such a lens assembly that may be operated in sectors.

Briefly, these and other objects of the present invention are accomplished by providing a rigid curved support member which defines an invivo target region. The convex outer surface of the curved support member has a plurality of generally planar mounting facets formed thereon. A plurality of electric to ultrasonic transducers are mounted on outer surface of the support member. Each transducer has an inner mounting face which is generally planar for mounting onto one of the mounting facets. The major dimension of each transducer extends generally parallel to the underlying mounting facet, and the minor dimension extends generally normal to the underlying mounting facet. In addition, each transducer has an outer contact face for connection to a voltage. An electrical connector establishes an electric field across each transducer between the outer contact face and the inner mounting face for conversion into ultrasonic energy. The concave inner surface on the curved support has a plurality of focusing surfaces thereon, one focusing surface immediately opposed to each mounting facet on the outer surface. Each focusing surface forms an ultrasonic unit with the opposed mounting facet and the transducer mounted thereover to focus the ultrasonic energy from that transducers.

BRIEF DESCRIPTION OF THE DRAWING

Further objects and advantages of the present lens assembly and the convergence of the ultrasonic energy will become apparent from the following detailed description and drawing in which.

Figure 1:
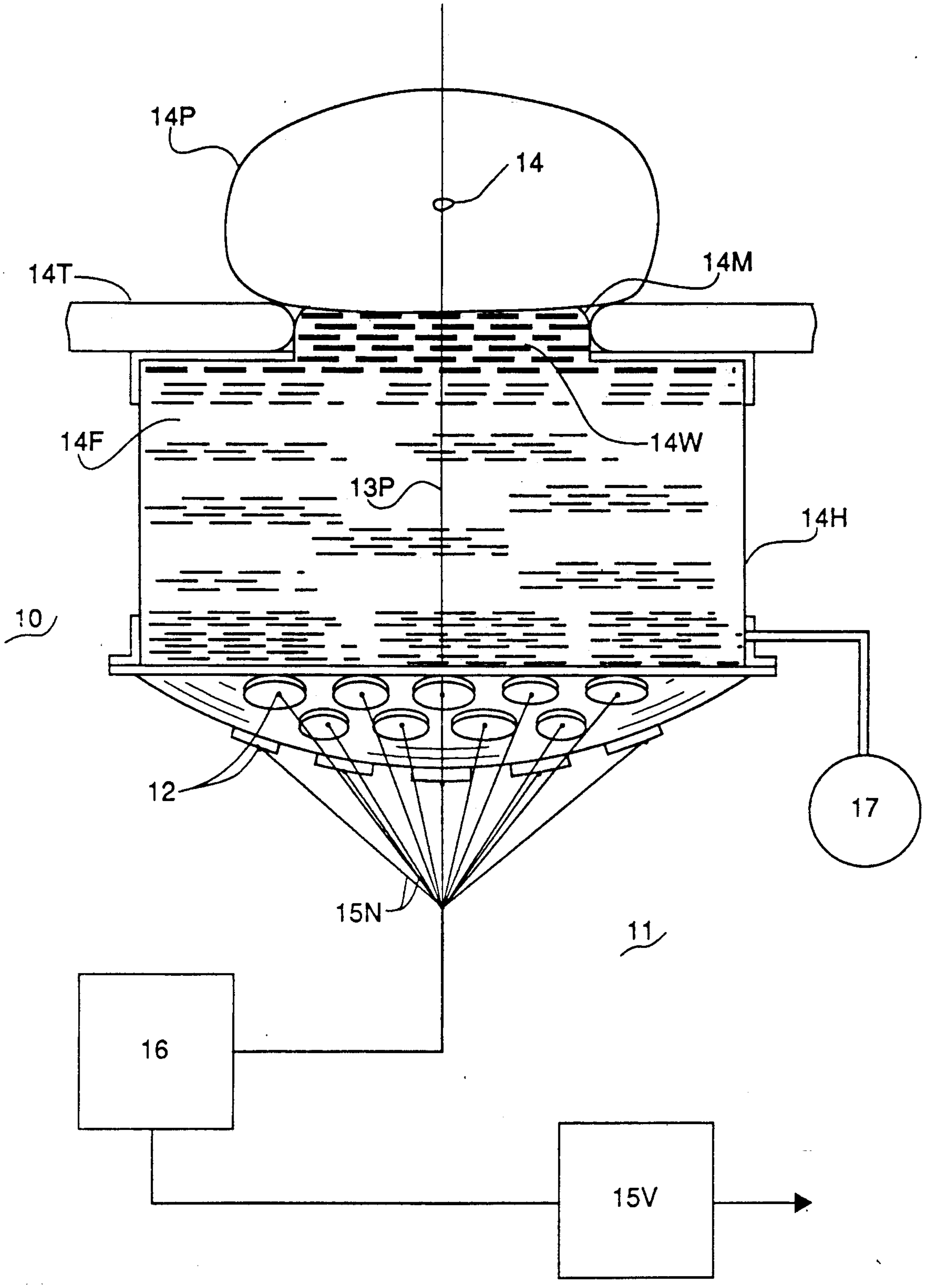
FIG. 1 is a schematic view of a general ultrasonic lithotripsy machine employing a high energy lens assembly.

Each element of the invention is designated by a two digit reference numeral. The first digit indicates the Figure in which that element is first disclosed or is primarily described. The second digit indicates like features and structural elements throughout the Figures. Some reference numerals are followed by a letter which indicates a subportion or feature of that element.

GENERAL EMBODIMENT (FIG. 1)

High energy ultrasonic device 10 has a lens assembly 11 formed by an array of electrical to ultrasonic transducers 12 mounted on the convex outer surface of rigid, bowl shaped support member 13. The contour of the support member defines a focal depth or invivo target region 14. Patient 14P on an adjustable table 14T is positioned proximate to energy window 14W so that the invivo treatment site coincides with the target region. The space between the lens assembly and the patient contains a suitable transmission fluid 14F such as water, oil or glycerin, within rigid housing 14H. Flexible membrane 14M over the energy window permits fluid-to-patient interface.

Crystal material within transducers 12 is periodically charged by a high voltage from voltage source 15 V. The charging voltage is applied to each transducer by suitable electrical distribution leads such as conductive network 15N which is connected to one terminal of the voltage. In the embodiment of FIG. 1, support member 13 under the transducers is conductive and functions as the inner distribution conductor connected to the other terminal of the voltage. The applied voltage establishes an electrical field across each transducer crystal. The transducers are discharged rapidly by switching system 16. The individual pulse of ultrasonic energy from each transducer merges into a collective pulse which converges toward the target region becoming highly concentrated.

Degassing system 17 continuously extracts gaseous material such as atmospheric air which has become dissolved or suspended in the transmission fluid. The concentrated ultrasonic energy passing through the fluid causes gaseous material to form bubbles which diffuse or scatter the ultrasonic waves.

MOUNTING FACETS (FIG. 2)

The rear or external side of support member 13 has a convex surface machined to provide a plurality of planar mounting facets 23F. Each facet has a normal center line 23N perpendicular to the plane of the facet. The facets are orientated so that the center lines pass through a common center of curvature 14C in target region 14. The support member is symmetrically curved about a primary axis 13P which is preferably the normal center line through center transducer 32P (see FIG. 3).

Figure 2:
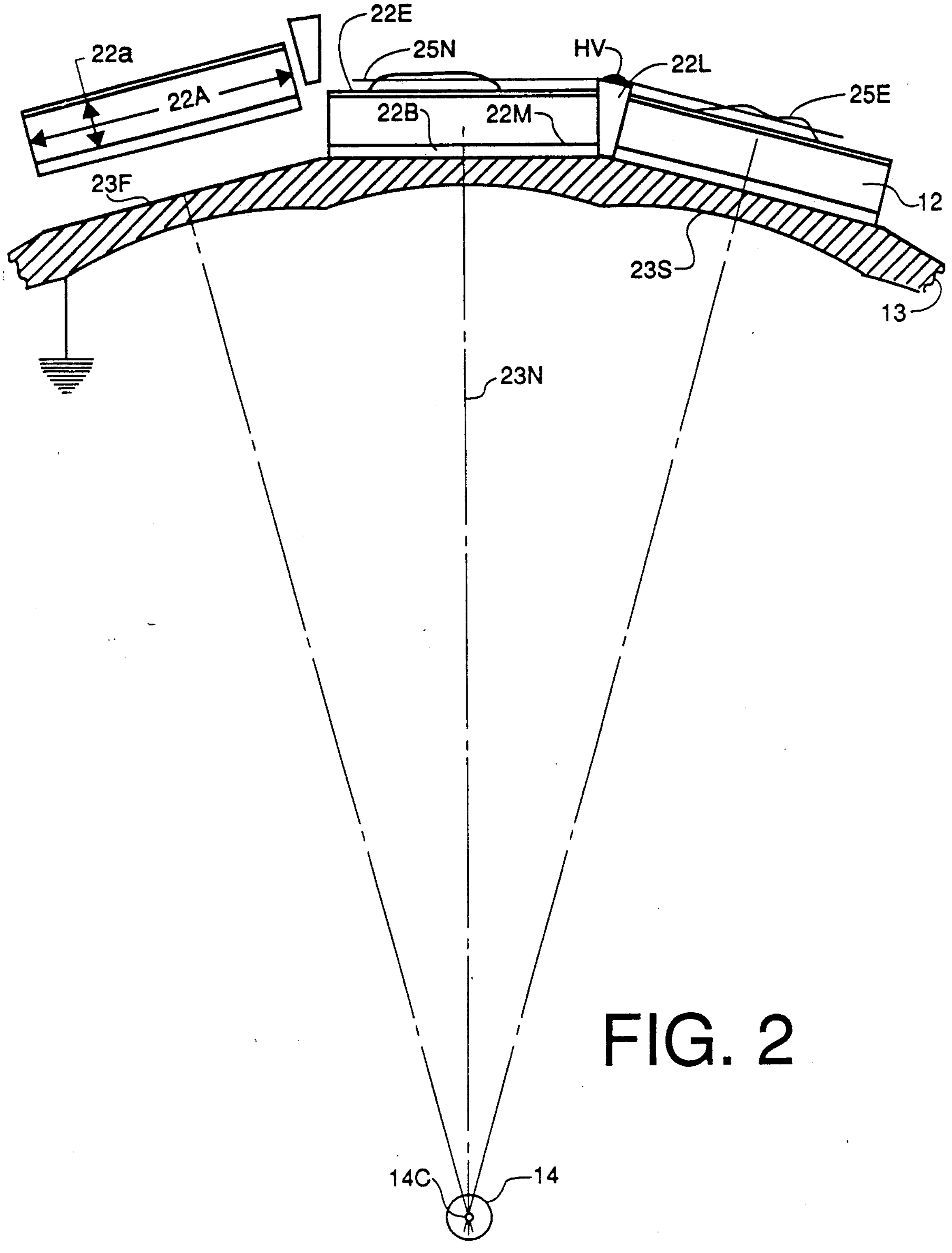
FIG. 2 is a fragmentary sectional view of a lens assembly showing the outer mounting facets and the inner focusing surfaces.

Each transducer 12 has an inner mounting face 22M which engages one of the mounting facets 23F along a bond line 22B. Each transducer has a rear or outer electrode face 22E which electrically engages conductive mesh 25N by means of a suitable conductive medium such as conductive epoxy 25E. In the embodiment of FIG. 2, the high voltage terminal (HV) of the charging voltage is connected to the conductive mesh, and the ground terminal is connected to the support member. Transducers 12 may be disk shaped with a major dimension 22A extending generally parallel to underlying mounting facet, and a minor dimension **22*a*** extending generally normal to the mounting facet.

The mounting face of each transducer is generally planar to match the flat surface of the underlying mounting facet producing a uniform thin bond line 22B. Thin bonds lines establish stronger bonds with a longer service life. In addition, thin bond lines have less electrical resistance and will dissipate less voltage during charging and discharging of the transducers.

Voltage lost across the bond line reduces the applied high voltage from source 15 V that actually appears across the transducer crystals. The bond line voltage loss may be minimized further by the addition of a conductive additive such as silver to the epoxy. A conductive bond line may function as the inner electrical distribution conductor for non-conductive support members formed of insulative materials such as plastics or ceramics.

FOCUSING SURFACE (FIG. 2)

The internal or target side of support member 13 is a large concave surface with a plurality of smaller concave lenses or focusing surfaces 23S machined thereon. Each of these small focusing lens is centered in front of an opposed flat mounting facet on the other side of the support member, and is symmetrical about an axis of symmetry which passes through common point 14C. Each lens 23S focuses the individual pulse of energy from a single transducer at target region 14, where the individual pulses merge into an intense collective pulse.

The diameter of the concave lenses is much less than the focal depth of the support member, which reduces edge delay within an individual pulse. That is, the path length of the energy from the edge of a transducer, through the edge of the lens, to the target region is only slightly greater than the path length of the energy from the center of the transducer, through the center of the lens. This relative size and path length relationship permits the use of true spherical sector surfaces for the focusing surface without significant compromise of the in phase condition. If preferred, the lenses may be slightly oblate to further enhance the in phase relationship within the collective pulse. The curve of the support member may also be true or oblate depending on the correction requirements.

SNELL'S LAW

The radius of curvature of each spherical focusing surface is located along its axis of symmetry, and may be calculated from Snell's law for refraction of ultrasonic waves in a specific support member material and transmission medium:

$$Rlen = (Rsup)\,(1 - Vm/Vs)$$

where

Rlen = radius of curvature of the focusing surface
Rsup = radius of curvature of the support member
Vm = sonic velocity in transmission medium
Vs = sonic velocity in support member material The radius of curvature of the concave focusing surface is always less than the radius of curvature of the support member because of a the relative sonic velocities Vm and Vs. However, the ultrasonic energy is focused at a common center of curvature 14C even though the center of curvature of the focal surface falls short of the target region.

ULTRASONIC UNITS

An independent ultrasonic unit is formed by each focusing surface, the immediately opposed mounting facet, and the transducer mounted thereover for generating an individual pulse of ultrasonic energy to be focused at the target region. The transducer in each unit is preferably centered on the underlying facet; and the axis of symmetry for the focusing surface in each unit is coincident with the normal center line of the opposed mounting facet. The unit focal point of each focusing surface is on the axis of symmetry thereof at a distance of Rlen.

The contour of the support member determines the distance from the support member to the target region. The size of the target region and the intensity of the ultrasonic energy focused therein is determined by the machine tolerances of the mounting facets and focusing surfaces. In general, a lens assembly with smaller target region tends to erode the invivo target down to a smaller residual size. A target region of about 1.5–2 mm is suitable for many applications.

HEXAGON PATTERN EMBODIMENT (FIG. 3)

Figure 3:
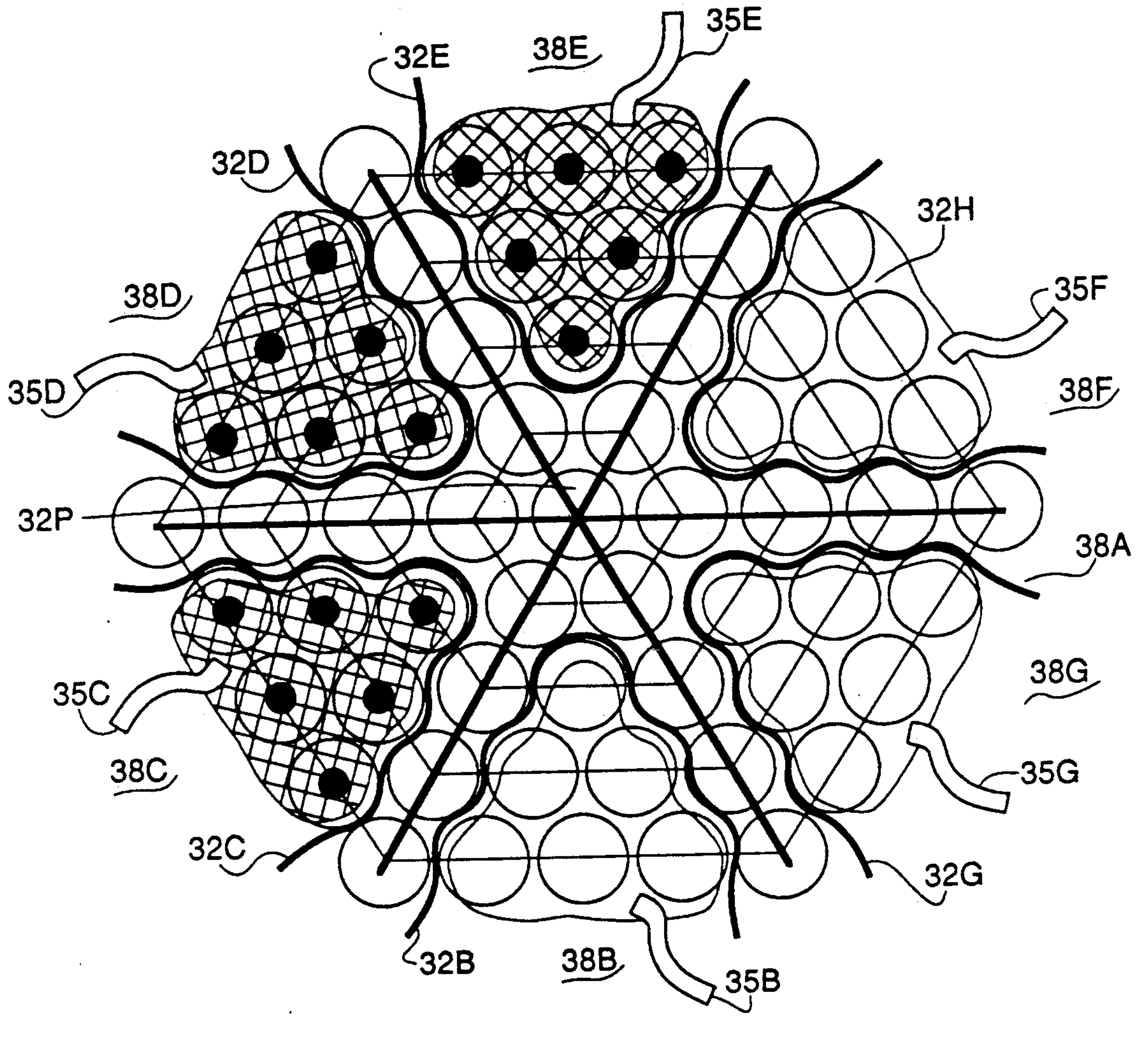
FIG. 3 is a rear plan view of the transducer array showing the transducer centers arranged in a pattern of concentric hexagons with interstitial space between adjacent transducers.
Figure 4:
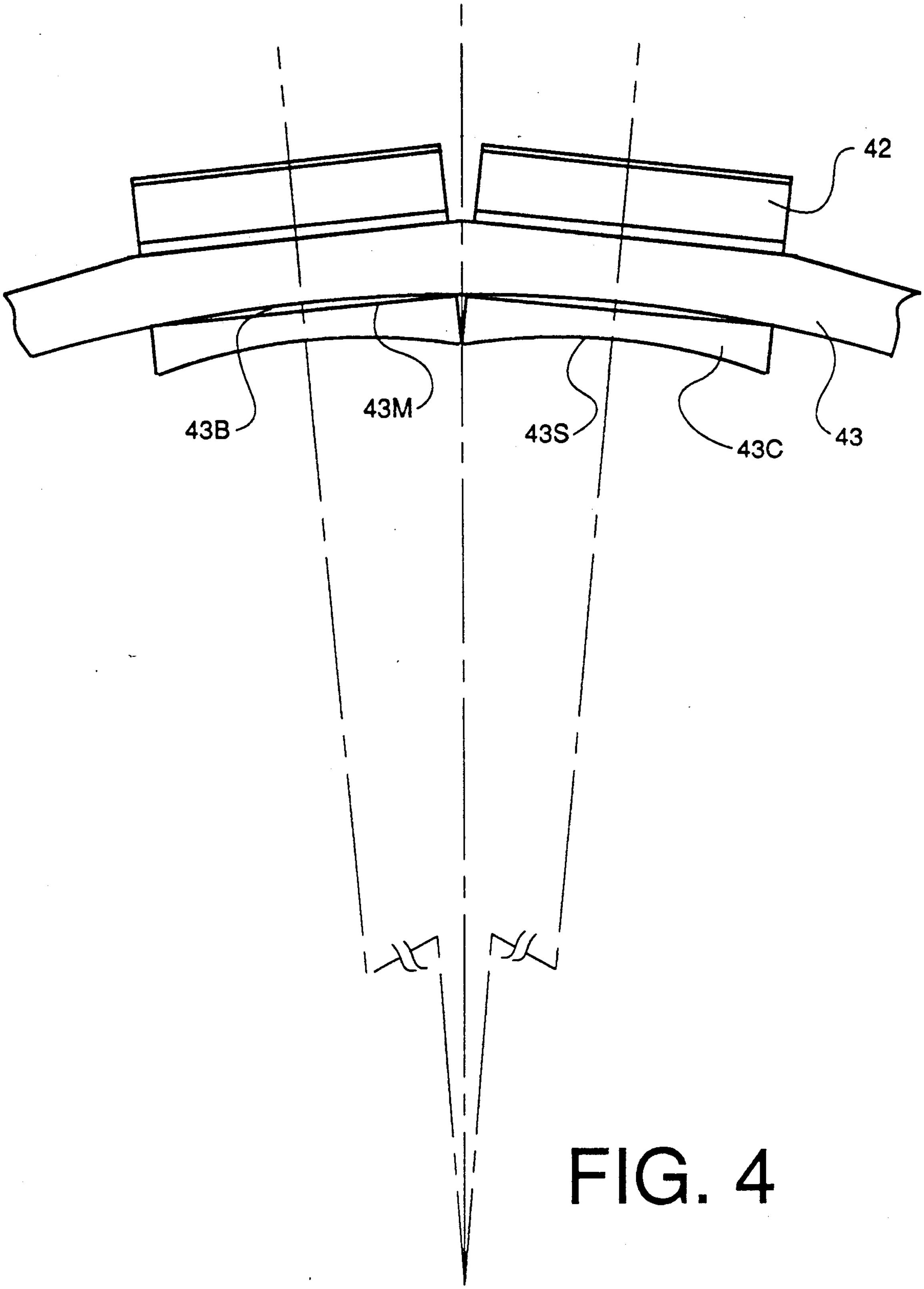
FIG. 4 is a sectional view of a transducer array having focusing caps mounted on the inside of the lens support in place of the machined surfaces of FIG. 2.

The transducer centers may be arranged in a pattern of concentric hexagons of increasing size around a center position 32P which may be a transducer or an adit port for an ultrasonic imaging probe. In the embodiment of FIG. 3, the transducers are round with their centers forming the hexagons. The number of transducers in each hexagon increases by an increment of six. The first hexagon around the center position has 6 transducers, the second hexagon has 12 transducers, etc.

Adjacent transducers within the same hexagon are separated by intra-hexagon interstitial space 32H. Adjacent transducers of bordering hexagons are separated by inter-hexagon interstitial space 32B. The lens assembly is curved, not flat: causing the interstitial spaces to decrease as the size of the hexagons increase.

The interstitial spaces have a wedge shaped cross section as shown in FIG. 2. The spaces are narrower along the bottom near the support member, and wider at the top near the outer contact face of the transducers. A suitable resilient cushioning material such as wedge shaped lattice 22L extending throughout the transducer array may be employed to prevent adjacent transducers from banging against each other during generation of the ultrasonic energy. The cushioning material may be an insulator for isolating the high voltage on the outer contact face of the transducer from ground on the support member. Without suitable insulation, fringe breakdown may occur around the periphery of the transducer.

SECTOR OPERATION

The transducers may be operated as a single array, or they may be sectored to operate as several smaller arrays as shown in the embodiment of FIG. 3. Center array 38A has three intersecting lines of transducers formed by the transducers at the vertices of the hexagons. Six symmetrical side arrays 38B, 38C, 38D, 38E, 38F and 38G are formed by the transducers between the lines of subarray 38A. The transducers of the center array are connected together and connected to the high voltage by three strip conductors 35A. Each of the six side arrays has a separate mesh and connector 35B, 35C, 35D, 35E, 35F and 35G for the high voltage, and may be activated independently. Insulating dividers 32B, 32C, 32D, 32E, 32F and 32G extend along the interstitial space between the sectors to isolate the high voltage applied to the activated sector from the inactivated sectors.

FOCUSING CAP EMBODIMENT (FIG. 4)

Focusing caps 43C mounted along the inner concave surface of support member 43 may be employed to provide the focusing surface for the ultrasonic energy from transducer 42 in place of the machined focusing surfaces 23S of the embodiment of FIG. 2. The caps may be easily formed or machined prior to mounting within the lens assembly. The focusing surface may be either a true sphere or slightly oblate. Mounting surface 43M of the cap may be flat as shown or may be curved to facilitate bonding with the adjacent inner surface of the support member. The cap may be formed of any suitable material with an acoustic impedance close to the acoustic impedance of the support member. The material of the cap may be selected to enhance the acoustically match between the support and the transmission medium. Preferably, the bond material within cap-to-support bond line 43B is thin to promote acoustical transfer.

SPECIFIC EMBODIMENT

The following particulars of lens assembly 11 are given as an illustrative example of the present invention:

Support Member 13—sector of 16″ (40.6 cm) true sphere, area of about 1200 sq cm, made of aluminum with an anodized surface.

Mounting Facets 23F—about 2″ (5.08 cm) in diameter.

Transducers 12—60 disks 2″ (5.08 cm) in diameter and one half inch (1.27 cm) thick, made of ceramic piezo electric material such as lead zirconate and capable of sustaining an electric field of about 20 volts per mil of thickness.

Focusing Surface 23S—sector of a true sphere having curvature of about 12″ (30.5 cm) calculated from Snell's law:

$$Rlen = Rsup\,(1 - Vw/Va)$$

where

Rlen = radius of curvature of the focusing face
Rsup = radius of curvature of support surface
Vw = sonic velocity of transmission water
Va = sonic velocity of aluminum support.

Insulative Cushion 22L—nylon wedge, 100 mils (0.256 cm) across the top, 60 mils (0.154 cm across the bottom).

High Voltage—about 10,000 volts.

The values, dimensions and material given above are not intended as defining the limitations of the invention. Numerous other constructions and configurations are possible.

INDUSTRIAL APPLICABILITY

It will be apparent to those skilled in the art that the objects of this invention have been achieved by providing a lens assembly which produces less phase loss between the individual energy pulse from the transducers. The individual pulses arrive at the target region in a tighter group closer in time. Because of this enhanced phase condition, the lens assembly is more efficient and delivers the maximum pulse intensity with minimum operating voltage and lens area. The support member and focusing lenses may be simple curves having a true spherical surface to provide a simpler and less expensive lens assembly.

CONCLUSION

Clearly various changes may be made in the structure and embodiments shown herein without departing from the concept of the invention. Further, features of the embodiments shown in the various Figures may be employed with the embodiments of the other Figures.

Therefore, the scope of the invention is to be determined by the terminology of the following claims and the legal equivalents thereof.

We claim as our invention:

1. A high energy ultrasonic device for in vivo treatment, comprising:

- a rigid curved support means for defining an in vivo target region;
- a convex outer mounting surface on the curved support means having a plurality of generally planar mounting facets formed thereon;
- a plurality of electric to ultrasonic transducers mounted on the convex outer surface of the curved support means, each of said transducers having an inner mounting face which is generally planar for mounting onto one of the mounting facets, and each of said transducers having an outer contact face for connection to an electric voltage source;
- each of said transducers having a major dimension extending generally parallel to the underlying mounting facet and a minor dimension extending generally normal to the underlying mounting facet;
- electrical connector means for establishing an electric field across each of said transducers between the outer contact face and the inner mounting face for conversion into ultrasonic energy; and a concave inner surface on the curved support means having a plurality of focusing means thereon, each one of said focusing means immediately opposed to each of said mounting facets on the outer surface, each of said focusing means forming an ultrasonic unit with each of the opposed mounting facets and each of the transducers mounted thereover to focus the ultrasonic energy from each of the transducers.

2. The ultrasonic device of claim 1 wherein each of said transducer-facet-focusing ultrasonic units is identical to each of the other ultrasonic units.

3. The ultrasonic device of claim 2 wherein each of the transducers is a round disk.

4. The ultrasonic device of claim 3 wherein the round disk transducers are arranged in a pattern of concentric hexagons of increasing size.

5. The ultrasonic device of claim 4 wherein the pattern of concentric hexagons increases in size in increments of six transducers.

6. The ultrasonic device of claim 5 further comprising:

a resilient cushion in the interstitial space between adjacent transducers.

7. The ultrasonic device of claim 4 wherein the pattern of concentric hexagons has a first hexagon containing 6 transducers, and a second hexagon containing 12 transducers, and a third hexagon containing 18 transducers, and a fourth hexagon containing 24 transducers.

8. The ultrasonic device of claim 6 wherein the pattern of concentric hexagons has a center transducer inside the first hexagon.

9. The ultrasonic device of claim 4 wherein each disk transducer is separated from the adjacent transducers in the same hexagon forming an intra-hexagon interstitial space, and separated from the adjacent transducers in the bordering hexagons forming an inter-border interstitial space.

10. The ultrasonic device of claim 9 wherein the intra-hexagon interstitial space diminishes slightly for each larger hexagon.

11. The ultrasonic device of claim 1 wherein the support means is symmetrically curved about a primary axis which passes through the target region defined by the support means.

12. The ultrasonic device of claim 11 wherein the curved support means is a segment of a true sphere with the target region at the center of curvature thereof.

13. The ultrasonic device of claim 11 wherein the curved support means is a segment of an oblate sphere with the target region at the center thereof.

14. The ultrasonic device of claim 11 wherein the normal center axis of each of the mounting facets in each said ultrasonic unit passes through a common point in the target region defined by the curve of the support means.

15. The ultrasonic device of claim 14 wherein the focusing means in each said ultrasonic unit is a curved focusing surface for defining a unit focal point along the normal center axis of each said ultrasonic unit.

16. The ultrasonic device of claim 15 wherein the relationship between the radius of curvature of the focusing surface and the radius of curvature of the support means is approximately $$Rlen=(Rsup)\,(1-Vm/Vs)$$

where

Rlen = radius of curvature of the focusing surface,

Rsup = radius of curvature of the support means,

Vm = sonic velocity in transmission medium, and

Vs = sonic velocity in support means material.

17. The ultrasonic device of claim 15 wherein the curved focusing surface in each said ultrasonic unit is formed on the concave inner surface of the curved support means.

18. The ultrasonic device of claim 15, wherein the curved focusing surface comprises:

a plurality of focusing caps mounted on the concave inner surface of the curved support means proximate each of the mounting facets within each of the ultrasonic units, each said cap having an inner mounting surface for engaging the concave inner surface of the curved support means, and each said cap having a curved outer focal surface for defining a focal point along the center axis of each of the ultrasonic units.

19. The ultrasonic device of claim 15 wherein the curve of the focusing surface is a true sphere.

20. The ultrasonic device of claim 15 wherein the curve of the focusing surface is an oblate sphere.

21. The ultrasonic device of claim 1 wherein the electrical connector means further comprise, an outer electrode across the outer contact face of each transducer;

an inner electrode across the inner mounting face of each transducer;

outer distribution conductor means for connecting the outer electrode to one terminal of the electric voltage source; and inner distribution conductor means for connecting the inner electrode to the other terminal of the electric voltage source.

22. The ultrasonic device of claim 21 wherein the outer electrode is a conductive mesh extending over outer contact faces of the transducers on the convex mounting surface of the curved support means.

23. The ultrasonic device of claim 22 further comprising a conductive epoxy for cementing the conductive mesh to each of the outer contact faces of the transducers.

24. The ultrasonic device of claim 21 wherein the curved support means is conductive and forms the inner electrode.

25. The ultrasonic device of claim 24 wherein the curved support means is formed of aluminum.

26. The ultrasonic device of claim 24 wherein the curved support means is formed of aluminum with an anodized layer thereover.

27. The ultrasonic device of claim 21 wherein the transducers are bonded to the support means by an epoxy, and the inner electrode is formed by a conductive additive in the epoxy.

28. The ultrasonic device of claim 21 wherein the outer electrode is connected to the high voltage side of the electric voltage source, and the inner electrode is connected to the ground side of the electric voltage source.

29. The ultrasonic device of claim 21 wherein the plurality of transducers are divided into sectors with an inter-transducer space between adjacent sectors, and the outer distribution conductor means provides a separate connection from the one terminal of the electric voltage source to each transducer sector.

30. The ultrasonic device of claim 29 further comprising insulative divider means in the inter-transducer space between adjacent transducer sectors.

31. The ultrasonic device of claim 29 wherein the inter-transducer space has a wedge cross-section with the wide portion of the wedge proximate the outer electrode and the narrow portion proximate the inner electrode.

32. The ultrasonic device of claim 29 wherein the transducers are arranged in a pattern of hexagons of increasing size.

33. The ultrasonic device of claim 32 wherein the sectors further comprise a central sector formed by the transducers at the vertices of the hexagons in the pattern, and six side sectors formed by the transducers between the vertices.

* * * * *